United States Patent
Mikkola et al.

(10) Patent No.: US 11,753,592 B2
(45) Date of Patent: Sep. 12, 2023

(54) CONVERSION OF ALCOHOLS TO HYDROCARBONS USING A DUAL CATALYST SYSTEM COMPRISING BASIC OXIDE ON MIXED OXIDE OR MESOPOROUS CARRIER AND ETCHED METAL LOADED ZEOLITE CATALYST

(71) Applicant: Eco-Oil Miljöbränslen i Sverige AB, Skellefteå (SE)

(72) Inventors: Jyri-Pekka Mikkola, Umeå (SE); Ajaikumar Samikannu, Umeå (SE); Kent Vanklint, Skellefteå (SE); William Siljebo, Bjurholm (SE)

(73) Assignee: ECO-OIL MILJOBRANSLEN I SVERIGE AB, Skelleftea (SE)

( * ) Notice: Subject to any disclaimer, the term of this patent is extended or adjusted under 35 U.S.C. 154(b) by 0 days.

(21) Appl. No.: 16/063,609

(22) PCT Filed: Dec. 20, 2016

(86) PCT No.: PCT/SE2016/051296
§ 371 (c)(1),
(2) Date: Jun. 18, 2018

(87) PCT Pub. No.: WO2017/111691
PCT Pub. Date: Jun. 29, 2017

(65) Prior Publication Data
US 2018/0371328 A1 Dec. 27, 2018

(30) Foreign Application Priority Data
Dec. 22, 2015 (SE) .................... 1551699-0

(51) Int. Cl.
C10G 3/00 (2006.01)
B01J 29/44 (2006.01)
(Continued)

(52) U.S. Cl.
CPC ............ *C10G 3/45* (2013.01); *B01J 21/10* (2013.01); *B01J 21/12* (2013.01); *B01J 23/002* (2013.01);
(Continued)

(58) Field of Classification Search
None
See application file for complete search history.

(56) References Cited

U.S. PATENT DOCUMENTS

| 4,148,835 A | 4/1979 | Chen et al. |
| 4,621,164 A | 11/1986 | Chang et al. |

(Continued)

FOREIGN PATENT DOCUMENTS

| CN | 103827058 A | 5/2014 |
| GB | 1586845 A | 3/1981 |

(Continued)

OTHER PUBLICATIONS

Luo et al. "Zeolite-supported metal catalysts for selective hydrodeoxygenation of biomass-derived platform molecules" Green Chemistry. pp. 3744-3768. 2019 (Year: 2019).*

(Continued)

*Primary Examiner* — In Suk C Bullock
*Assistant Examiner* — Alyssa L Cepluch
(74) *Attorney, Agent, or Firm* — Porter Wright Morris & Arthur LLP (57) ABSTRACT

A method for converting an alcohol to hydrocarbons comprises two serially placed catalysts. The fraction of aromatics is reduced to desired levels. The method comprises: a) contacting the alcohol with a first catalyst on a carrier, said carrier is selected from a mixed oxide and a mesoporous carrier, said first catalyst comprises at least one basic oxide and optionally at least one selected from the group consisting of metals and metal oxides, then b) contacting the (Continued)

resulting mixture from step a) with a second catalyst wherein said second catalyst is an etched metal loaded zeolite catalyst wherein the etched metal loaded zeolite catalyst is manufactured with a method comprising etching with subsequent loading of metal onto the catalyst, wherein the metal is in the form of nanoparticles, and wherein at least two different metals are loaded onto the etched zeolite catalyst. The hydrocarbons are recovered and used for instance for fuel including gasoline, kerosene, diesel, and jet propellant, and jet fuel. Naturally, other uses of hydrocarbons should not be excluded.

20 Claims, 9 Drawing Sheets (51) Int. Cl.
| | |
|---|---|
| B01J 29/46 | (2006.01) |
| C07C 1/24 | (2006.01) |
| C07C 2/12 | (2006.01) |
| B01J 35/00 | (2006.01) |
| B01J 23/755 | (2006.01) |
| B01J 29/85 | (2006.01) |
| C07C 1/20 | (2006.01) |
| B01J 29/072 | (2006.01) |
| C10G 50/00 | (2006.01) |
| B01J 21/12 | (2006.01) |
| B01J 23/78 | (2006.01) |
| B01J 21/10 | (2006.01) |
| B01J 23/00 | (2006.01) |

(52) U.S. Cl.
CPC ............. *B01J 23/755* (2013.01); *B01J 23/78* (2013.01); *B01J 29/072* (2013.01); *B01J 29/44* (2013.01); *B01J 29/46* (2013.01); *B01J 29/85* (2013.01); *B01J 35/002* (2013.01); *B01J 35/0006* (2013.01); *C07C 1/20* (2013.01); *C07C 1/24* (2013.01); *C07C 2/12* (2013.01); *C10G 3/00* (2013.01); *C10G 3/44* (2013.01); *C10G 3/47* (2013.01); *C10G 3/48* (2013.01); *C10G 3/49* (2013.01); *C10G 3/62* (2013.01); *C10G 50/00* (2013.01); *B01J 2523/17* (2013.01); *B01J 2523/27* (2013.01); *B01J 2523/57* (2013.01); *B01J 2523/69* (2013.01); *B01J 2523/74* (2013.01); *B01J 2523/824* (2013.01); *B01J 2523/828* (2013.01); *B01J 2523/842* (2013.01); *B01J 2523/847* (2013.01); *C07C 2521/08* (2013.01); *C07C 2521/10* (2013.01); *C07C 2521/12* (2013.01); *C07C 2523/755* (2013.01); *C07C 2529/44* (2013.01); *C10G 2400/02* (2013.01); *C10G 2400/04* (2013.01); *C10G 2400/08* (2013.01); *Y02P 20/52* (2015.11); *Y02P 30/20* (2015.11)

(56) References Cited

U.S. PATENT DOCUMENTS

| | | | | |
|---|---|---|---|---|
| 4,665,268 A | * | 5/1987 | Lee | B01J 29/7034 |
| | | | | 585/640 |
| 4,885,405 A | * | 12/1989 | Dornhagen | C07C 41/09 |
| | | | | 568/698 |
| 5,188,996 A | * | 2/1993 | Huang | B01J 23/96 |
| | | | | 502/262 |
| 5,993,642 A | | 11/1999 | Mohr et al. | |
| 6,372,680 B1 | * | 4/2002 | Wu | B01J 29/005 |
| | | | | 502/64 |
| 7,722,825 B1 | | 5/2010 | Bozzano et al. | |
| 7,767,867 B2 | * | 8/2010 | Cortright | C01B 3/323 |
| | | | | 568/861 |
| 8,338,655 B2 | | 12/2012 | Chang et al. | |
| 2006/0025646 A1 | | 2/2006 | Fung et al. | |
| 2006/0063956 A1 | | 3/2006 | Kalnes et al. | |
| 2008/0216391 A1 | * | 9/2008 | Cortright | C07C 45/57 |
| | | | | 44/307 |
| 2010/0076233 A1 | * | 3/2010 | Cortright | C10G 45/08 |
| | | | | 585/331 |
| 2010/0179359 A1 | * | 7/2010 | Yeh | B01J 29/06 |
| | | | | 502/64 |
| 2010/0305376 A1 | * | 12/2010 | Rothaemel | C10G 3/54 |
| | | | | 585/319 |
| 2012/0178615 A1 | * | 7/2012 | Corma | B01J 29/44 |
| | | | | 502/64 |
| 2012/0178981 A1 | * | 7/2012 | Corma | B01J 29/06 |
| | | | | 585/532 |
| 2013/0261361 A1 | * | 10/2013 | Blommel | C07C 1/2078 |
| | | | | 585/322 |
| 2014/0114101 A1 | * | 4/2014 | Greene | C10G 3/42 |
| | | | | 585/329 |
| 2014/0171691 A1 | | 6/2014 | Kortan et al. | |
| 2014/0256010 A1 | | 9/2014 | Narula et al. | |
| 2014/0273146 A1 | | 9/2014 | Narula et al. | |
| 2015/0159099 A1 | * | 6/2015 | Luebke | C10L 1/06 |
| | | | | 585/252 |
| 2015/0191666 A1 | * | 7/2015 | Bradin | C10G 50/00 |
| | | | | 585/14 |
| 2015/0336856 A1 | * | 11/2015 | Suh | C07C 1/20 |
| | | | | 585/408 |
| 2017/0036197 A1 | * | 2/2017 | Kegnæs | B01J 35/0006 |

FOREIGN PATENT DOCUMENTS

| | | |
|---|---|---|
| JP | 54-12334 A | 1/1979 |
| WO | 2006/036293 A1 | 4/2006 |
| WO | 2011/162717 A1 | 12/2011 |
| WO | 2012/174205 A1 | 12/2012 |
| WO | 2014/137991 A1 | 9/2014 |

OTHER PUBLICATIONS

White et al. "Opportunities for Catalysis in the 21st Century" Basic Energy Scienes Advisory Committee Subpanel Workshop Report. 2002. (Year: 2002).*
Sugunan et al. "Acid-Base Properties and Catalytic Activity of ABO3 (Perovskite-type) Oxides Consisting of Rare Earth and 3d Transition Metals" Reaction Kinetics and Catalysis Letters vol. 62, No. 2, 327-332 (1997) (Year: 1997).*
Britannica Online Encyclopedia "Oxides". pp. 1-8. Published Sep. 6, 2015. Retrieved Mar. 27, 2020. (Year: 2015).*
Miyake, M., Dealumination of zeolites and clay minerals with SiCl4 or (NH4)2SiF6, Clay Minerals, vol. 22, pp. 367-371 (1987).
Zharova, P.A., Conversion of ethanol and glycerol to olefins over the Re and W-containing catalyst, Russian Chemical Bulletin, International Edition, vol. 64, No. 2, pp. 337-345 (Feb. 2015).
Official Action from corresponding Chinese Application No. 201680074548.8, dated Sep. 1, 2020, with English Translation.
Official Action from corresponding Japanese Application No. 2018-533727, dated Aug. 28, 2020, with English Translation.
Johan C. Groen et al, "Desilication: on the controlled generation of mesoporosity in MFI zeolites", Journal of Materials Chemistry, 16:2121-2131 (2006).

* cited by examiner

CONVERSION OF ALCOHOLS TO HYDROCARBONS USING A DUAL CATALYST SYSTEM COMPRISING BASIC OXIDE ON MIXED OXIDE OR MESOPOROUS CARRIER AND ETCHED METAL LOADED ZEOLITE CATALYST

TECHNICAL FIELD

The present invention relates generally to a process for converting alcohols to hydrocarbons and water. Moreover, the $CO_2$ obtained during the optional regeneration cycle of the catalyst bed, can be collected and used elsewhere as pure, bio-origin carbon dioxide. The hydrocarbons can, for instance, be used as fuels for combustion engines and other purposes.

BACKGROUND

Generally, it is desired to be able to convert alcohols into hydrocarbons for purposes including but not limited to fuels. In the past different approaches have been utilized. The worldwide bio-ethanol production and ethanol transformation to gasoline has raised considerable interest in the recent years concerning the demand for bio-renewable alternatives to petroleum based fuels and chemicals. Ethanol and many other alcohols (viz. e.g. glycerol) cannot easily be used as a motor fuel, posing several technical difficulties such as low energy efficiency, cold start-up problems, increased pollution level (due to the fact that catalytic converters common in modern automobiles are designed for hydrocarbon fuels and, in case of e.g. ethanol, also catalyze the formation of toxic acetaldehyde among other smog components) and engine corrosion etc, but there is the possibility of converting ethanol and other alcohols into gasoline range (and other) hydrocarbons by the use of zeolite materials.

The current science community is much focused on finding the alternative and renewable resources for future energy. In this context, bio-ethanol is considered to be the one of the renewable resources that can be derived from biomass either by thermo-chemical or biochemical processes. Catalytic conversion of ethanol to gasoline hydrocarbons has received much attention in the last two decades because of the possibilities of utilizing bio-ethanol for future energy requirements. In this context, ZSM-5 found to be the promising catalyst giving complete conversion of ethanol towards gasoline range hydrocarbons. However, several problems (economic viability, catalyst stability, minimizing the aromatic contents in the product, utilizing direct aqueous ethanol for the process etc.) need to be addressed before the up scaling of this process. In this process, coke formation and catalyst deactivation is the major problem and is mainly caused because of the micro porosity, strong acidity and mass transfer limitations etc. In this context, attempts have been made regarding changing the chemical and physical properties of ZSM-5 (acidity, crystal size, pore size and channel structure etc.) and optimizing the reaction parameters in order to obtaining a good yield of gasoline fraction. Reducing the crystal size and introducing mesopores to the ZSM-5 is one strategy to improve the durability of the catalyst by controlling the mass transfer limitations. Strategies on introducing the mesoporosity and reducing the crystal size of ZSM-5 have been attempted. However, the stability of ZSM-5 and reducing the formation of aromatic content on ethanol to gasoline process is still remaining a challenge.

US2014/0273146 and WO 2012/174205 disclose a method for converting an alcohol to a hydrocarbon suitable for fuel. It uses a metal-loaded zeolite.

WO 2014/137991 discloses a method for converting an alcohol to a hydrocarbon with lowered benzene content. A metal loaded zeolite catalyst is used. Also a benzene alkylation catalyst is utilized. It should be noted that the metal loaded zeolite catalyst is manufactured so that metal is loaded throughout the material and not only on the surface.

U.S. Pat. No. 5,993,642 discloses a process for converting hydrocarbons using a zeolite as a catalyst.

Clay Minerals (1987) 22, 367-371 DEALUMINATION OF ZEOLITES . . . discloses a method to treat a zeolite.

U.S. Pat. No. 4,148,835 discloses a method to convert alcohols to hydrocarbons.

U.S. Pat. No. 4,621,164 discloses a process for converting ethanol to gasoline-boiling-range hydrocarbons by contact in the vapor phase at dehydrating temperature with a bifunctional zeolite catalyst in the presence of an equimolar proportion of water.

U.S. Pat. No. 8,338,655 discloses a process for converting a dilute ethanol solution to liquid hydrocarbon fuels such as LPG and gasoline by preferentially driving-off the ethanol molecules in the solution across the liquid-air interface and streaming same into a heating and catalytic reacting system maintained at the conversion conditions.

Russian Chemical Bulletin, International Edition, Vol. 64, No. 2, pp. 337-345, February, 2015 discloses a catalytic conversion of a mixture of ethanol and glycerol over Re—W/$Al_2O_3$ catalyst.

WO 2011/162717 discloses a method of producing alkenes by dehydration of a mixture of alcohols using a metal-modified zeolite, wherein the method comprises providing two or more alcohols; contacting the mixture with a catalyst, wherein the catalyst is a metal-modified zeolite; and reacting the mixture in a temperature range of about 350 to about 500° C., thereby producing the alkenes. It is for instance disclosed that a zeolite is treated in 0.2M NaOH at 80° C. during 24 hours before application of metal.

SUMMARY

It is an object of the present invention to obviate at least some of the disadvantages in the prior art and provide an improved method for converting alcohols to hydrocarbons.

In a first aspect there is provided method for converting an alcohol to hydrocarbons, said method comprising the steps of:
a) contacting the alcohol with a first catalyst on a carrier, where the carrier is a mixed oxide carrier or mesoporous carrier, said first catalyst comprises at least one basic oxide and optionally at least one selected from the group consisting of metals and metal oxides,
b) contacting the resulting mixture from step a) with a second catalyst wherein said second catalyst is an etched metal loaded zeolite catalyst wherein the etched metal loaded zeolite catalyst is manufactured with a method comprising a step of etching with subsequent loading of metal onto the catalyst, wherein the metal is in the form of nanoparticles, and wherein at least two different metals are loaded onto the etched zeolite catalyst,
c) recovering the hydrocarbons resulting from the reaction.

In a second aspect there is provided a hydrocarbon manufactured according to the method described above.

In a third aspect there is provided an apparatus for performing the method described above, said apparatus comprising a first part and a second part, connected so that a feed of alcohol entering the apparatus first comes into contact with said first part, and the resulting mixture comes into contact with said second part, said first part comprises a first catalyst on a carrier, said carrier is selected from a mixed oxide and a mesoporous carrier, said first catalyst comprises at least one basic oxide and optionally at least one selected from the group consisting of metals and metal oxides, said second part comprises a second catalyst wherein said second catalyst is an etched metal loaded zeolite catalyst wherein the etched metal loaded zeolite catalyst is manufactured with a method comprising a step of etching with subsequent loading of metal onto the catalyst, wherein the metal is in the form of nanoparticles, and wherein at least two different metals are loaded onto the etched zeolite catalyst.

Further aspects and embodiments are defined in the appended claims, which are specifically incorporated herein by reference.

Advantages include that that the invention reduces problems with coke formation in the catalyst, problems with long term stability, and problems with aromatic hydrocarbons in the end product. The stability of the catalyst is improved over prolonged reaction times. The amount of benzene, aromatics and polyaromatics are reduced.

The obtained reaction products have the properties and the qualities similar to that of commercial petrol.

Further different catalysts connected after each other in series provide a broader range of hydrocarbons as products and further possibilities to control the end-products.

The water produced in the process can if desired be utilized for any useful purpose. For instance, the water can be distilled with for instance fractional distillation and optionally be purified with active carbon in order to remove residual hydrocarbons.

Yet another advantage is that the process is not so sensitive for variations in the water content in alcohol mixtures serving as raw material for the process.

Excess heat generated during the process can be used to generate power and/or for district heating or for other useful purposes.

BRIEF DESCRIPTION OF THE DRAWINGS

The invention is now described, by way of example, with reference to the accompanying drawings, in which.

DETAILED DESCRIPTION

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

As used herein, the term "about" generally indicates within ±10% of the indicated value. For example, in its broadest sense, the phrase "about 100° C." means 100° C.±10%, which indicates 100±10° C. i.e. the range 90-110° C.

All percentages and ratios are calculated by weight unless otherwise clearly indicated.

The term "alcohol", as used herein, refers to a single alcohol or a mixture of two or more alcohols, and encompasses aqueous solutions of one or more water soluble alcohols. Most notable examples of alcohols considered herein include but are not limited to ethanol, n-butanol (i.e., butanol), and isobutanol. In different embodiments, the alcohol can be ethanol, or butanol, or isobutanol, or a combination thereof. Other alcohols include n-propanol, isopropanol, sec-butanol, t-butanol, n-pentanol, isopentanol (isoamyl alcohol) and glycerol. Examples of mixtures of alcohol is a mixture with an alcohol concentration of no more than about 20 wt %, 15 wt %, 10 wt %, or 5 wt %. In some embodiments, the stream is concentrated in alcohol (for example, of at least or up to 20%, 25%, 30%, 40%, 50%, 60%, 70%, or 80 wt %) before contacting the stream with the catalyst. In yet other embodiments, alcohol in the fermentation stream is selectively removed from the fermentation stream, such as by distillation, to produce a substantially pure form of alcohol as the feedstock. In still other embodiments, the alcohol is dewatered to near azeotropic ethanol (e.g., 92-94 wt % ethanol) or completely dewatered into 100 wt % alcohol before contacting with the catalyst.

The term "hydrocarbon", as used herein, refers to a single hydrocarbon compound or a mixture of two or more hydrocarbon compounds. Although a wide variety of hydrocarbon product can be produced by the instant method, the hydrocarbon primarily considered herein is typically saturated, and more particularly, in the class of alkanes, which may be straight-chained, or branched, or a mixture thereof, particularly when the hydrocarbon product is to be used as a fuel. The alkanes particularly desired herein include those containing at least four, five, or six carbon atoms, and up to twelve, fourteen, sixteen, seventeen, eighteen, or twenty carbon atoms. Examples of straight-chained alkanes include but are not limited to n-butane, n-pentane, n-hexane, n-heptane, n-octane, n-nonane, n-decane, n-undecane, n-dodecane, n-tridecane, n-tetradecane, n-pentadecane, n-hexadecane, n-heptadecane, n-octadecane, n-nonadecane, and n-eicosane. Examples of branched alkanes include but are not limited to isobutane, isopentane, neopentane, isohexane, 3-methylpentane, 2,3-dimethylbutane, 2,2-dimethylbutane, 2-methylhexane, 3-methylhexane, 2,2-dimethylpentane, 2,3-dimethylpentane, 2,4-dimethylpentane, 3,3-dimethylpentane, 2-methylheptane, and 2,2,4-trimethylpentane (isooctane). Some other hydrocarbon products typically produced by the instant conversion method include olefins (i.e., alkenes, such as, for example, ethylene, propylene, n-butene, and/or isobutene) and aromatics (for example, naphthalene, benzene, toluene, and/or xylenes).

The hydrocarbon product particularly considered herein is a mixture of hydrocarbon compounds useful as for instance a fuel or as a blendstock in a fuel. The mixture of hydrocarbon compounds produced herein preferably substantially corresponds (e.g., in composition and/or properties) to a known petrochemical fuel, such as petroleum, or a fractional distillate of petroleum. Some examples of petrochemical fuels include gasoline, kerosene, diesel, and jet propellant, jet fuel, (e.g., JP-8 and Jet A-1). Like hydrocarbon fuel grades in current use, the mixture of hydrocarbon compounds produced herein can, in some embodiments, be predominantly or exclusively composed of alkanes, alkenes, aromatics, or a mixture thereof. The raw hydrocarbon product, produced by the instantly described method, is in one embodiment fractionated by distillation into different fuel grades, each of which is known to be within a certain boiling point range.

Depending on the final composition of the hydrocarbon product, the product can be directed to a variety of applications, including, for example, as precursors for plastics, polymers, and fine chemicals. The process described herein can advantageously produce a range of hydrocarbon products that differ in any of a variety of characteristics, such as molecular weight (i.e., hydrocarbon weight distribution), degree of saturation or unsaturation (e.g., alkane to alkene ratio), and level of branched or cyclic isomers.

In a first aspect there is provided method for converting an alcohol to hydrocarbons, said method comprising the steps of:
a) contacting the alcohol with a first catalyst on a mesoporous carrier, said first catalyst comprises at least one basic oxide and optionally at least one selected from the group consisting of metals and metal oxides,
b) contacting the resulting mixture from step a) with a second catalyst wherein said second catalyst is an etched metal loaded zeolite catalyst wherein the etched metal loaded zeolite catalyst is manufactured with a method comprising a step of etching with subsequent loading of metal onto the catalyst, wherein the metal is in the form of nanoparticles, and wherein at least two different metals are loaded onto the etched zeolite catalyst,
c) recovering the hydrocarbons resulting from the reaction.

In an alternative embodiment a non-etched metal loaded zeolite catalyst is used. This embodiment also works, but the quality of the hydrocarbons becomes better if an etched metal loaded catalyst is used.

The fact that the raw material is first contacted with a first catalyst and then a second catalyst can be realized either so that there is a first catalyst in one reactor and then a second catalyst in a second reactor. An alternative approach is one elongated reactor with a first part and a second part, for instance an elongated tube where the first catalyst resides in the first part and the second catalyst resides in the second part, optionally there is a delimitation between the two parts.

Thus there is in one embodiment provided a two stage reactor system where two reactor beds are connected in series one after the other.

In one embodiment the temperature in step a) is in the range 300-550° C., preferably 350-450° C.

In one embodiment the temperature in step b) is in the range 300-500° C., preferably 300-400° C.

In one embodiment the mesoporous carrier of the first catalyst is not a zeolite but a mixed oxide. In an alternative embodiment the mesoporous carrier of the first catalyst is a zeolite.

In one embodiment the mesoporous carrier of the first catalyst comprises at least one selected from the group consisting of $Al_2O_3$, and $SiO_2$—$Al_2O_3$.

In one embodiment the mesoporous carrier of the first catalyst comprises at least one selected from the group consisting of SAPO-34, and SBA-15.

In one embodiment the metal in the first catalyst is at least one selected from the group consisting of Pt, Re, W, Ta, Pd, and Ni.

In one embodiment the first catalyst comprises MgO. Ni (for example, 2 wt-%) on amorphous silica-alumina ($SiO_2$—$Al_2O_3$) is a very good dehydration catalyst working well as the first catalyst. $SiO_2$—$Al_2O_3$ with Ni, i.e. Ni—$SiO_2$—$Al_2O_3$ as the first catalyst and Meso ZSM-5 with Cu as the second catalyst give a low amount of aromatics. For instance, one example with the first catalyst in a first reactor being Ni—$SiO_2$—$Al_2O_3$ and the second catalyst in a second reactor connected in series being Cu/Meso ZSM-5 gave 29.0 vol % aromatics (meeting the requirement of the European standard of not more than 35.0 vol % regarding aromatics).

In one embodiment the first catalyst comprises at least one metal selected from the group consisting of La, Ga, In, and Al.

In one embodiment the first catalyst comprises $LaNiO_3$. In one embodiment the first catalyst comprises Ni—$SiO_2$—$Al_2O_3$. Combinations of Ni—$SiO_2$—$Al_2O_3$ and $LaNiO_3$ are encompassed (as all combinations). In one embodiment the first catalyst comprises $LaNiO_3$ and Ni—$SiO_2$—$Al_2O_3$ in a weight ratio ($LaNiO_3$/Ni—$SiO_2$—$Al_2O_3$) in the interval 0.05-0.25. The embodiment with a mixture of $LaNiO_3$ and Ni—$SiO_2$—$Al_2O_3$ as the first catalyst has the advantage of giving a lower amount of olefins. For instance, one example with the first catalyst in a first reactor being $LaNiO_3$ and Ni—$SiO_2$—$Al_2O_3$ in a ratio 0.125 and the second catalyst in a second reactor connected in series being Cu/Meso ZSM-5 gave 18.0 vol % olefins (meeting the requirement of the European standard of not more than 19.0 vol % regarding olefins).

In one embodiment alcohol is added not only to the first catalyst in step a), but also to the second catalyst in step b) as an additional reactant together with the resulting mixture from step a). Thus a mixture of the result from step a) and newly added alcohol is fed to the second catalyst in step b). In one embodiment an amount of alcohol is added to the resulting mixture from step a). I.e. before it is fed to the second catalyst in step b).

In one embodiment an amount of the resulting mixture from step b) is recycled to at least one selected from the first catalyst and the second catalyst. In one embodiment the resulting mixture form step b) is recycled in a fraction of 1-50 wt % calculated on the resulting mixture from step b). In this embodiment the material which has been contacted with the second catalyst is fed to the first catalyst and/or the second catalyst as a recycle step.

In one embodiment the etching step during manufacture of the second catalyst is performed under basic conditions with a pH above 8.

In one embodiment the etching step during manufacture of the second catalyst is performed with NaOH.

In one embodiment the etching step during manufacture of the second catalyst is performed during a period in the interval from 5 minutes to 5 hours.

In one embodiment the etching step during manufacture of the second catalyst is performed at a temperature from 20-95° C.

In one embodiment the metal in the second catalyst is an alloy comprising at least two metals.

In one embodiment the metal in the second catalyst is at least two different metals. In one embodiment the metal in the second catalyst is at least one metal selected from the group consisting of Zn, Fe, Cu, Ni, Au, Pt, Pd, Ir, Rh, Co, Os, Re, and Ru. In one embodiment the metal in the second catalyst is at least one metal selected from the group consisting of Cu, Fe and Zn, Pd, and Pt.

In one embodiment the zeolite in the second catalyst is an aluminosilicate zeolite belonging to the pentasil family of zeolites.

In one embodiment the zeolite in the second catalyst is ZSM-5 or modified ZSM-5.

In one embodiment the alcohol is a primary alcohol.

In one embodiment the alcohol comprises at least one selected from the group consisting of methanol, ethanol, propanol, n-propanol, isopropanol and glycerol.

In one embodiment the alcohol comprises ethanol. In one embodiment the alcohol comprises ethanol and glycerol.

In one embodiment the alcohol is purified before step a) to remove at least one substance selected from the group consisting a substance originating from a fermentation process, sugars, sulphur, phenols, and cell residues.

In one embodiment the conversion of an alcohol to hydrocarbons is a continuous process. In an alternative embodiment the conversion of an alcohol to hydrocarbons is a batch process.

In one embodiment at least one of the first catalyst and the second catalyst is regenerated.

In one embodiment the first catalyst is residing in a first compartment and the second catalyst is residing in a second compartment. The first catalyst is in this embodiment in a first reactor (first compartment) and the second catalyst is in a second reactor (second compartment) and the reactors (compartments) are connected in series so that the alcohol is fed to the first reactor and the product exiting from the first reactor is fed to the second reactor. (Not ruling out that additional alcohol may be added to the product from the first reactor.)

In an alternative embodiment the first catalyst is residing in a first part of a compartment and wherein the second catalyst is residing in a second part of the same compartment and wherein first and second parts are located so that the alcohol first comes into contact with the first catalyst and then comes into contact with the second catalyst. One example of such an embodiment is one extended tubular reactor (compartment) wherein a first part comprises the first catalyst and a second part comprises the second catalyst. Then the alcohol flows to the first part and then the product from the first part flows to the second part. One example is a tube with one end comprising the first catalyst and a second end comprising the second catalyst. Then the alcohol flows in the tube and comes into contact with the first catalyst and then the products from the first catalyst flow further in the tube and comes into contact with the second catalyst. Such an embodiment also does not rule out that additional alcohol may be added to the products from the first catalyst before contacting with the second catalyst.

In a second aspect there is provided a hydrocarbon manufactured according to the method described above.

In one embodiment the hydrocarbon is a constituent in gasoline. In one embodiment the hydrocarbon is a constituent in diesel.

In one embodiment the hydrocarbon is a constituent in jet fuel.

In a third aspect there is provided an apparatus for performing the method described above, said apparatus comprising a first part and a second part, connected so that a feed of alcohol entering the apparatus first comes into contact with said first part, and the resulting mixture comes into contact with said second part, said first part comprises a first catalyst on a mesoporous or mixed oxide carrier, said first catalyst comprises at least one basic oxide and optionally at least one selected from the group consisting of metals and metal oxides, said second part comprises a second catalyst wherein said second catalyst is an etched metal loaded zeolite catalyst wherein the etched metal loaded zeolite catalyst is manufactured with a method comprising a step of etching with subsequent loading of metal onto the catalyst, wherein the metal is in the form of nanoparticles, and wherein at least two different metals are loaded onto the etched zeolite catalyst.

In one embodiment said first part is in thermal contact with said second part. Thus the exothermal reaction in the second part can be utilized to promote the slightly endothermal reaction in the first part.

In one embodiment said apparatus comprises parts which at least partially coated with copper (with possible tantalum coating for better corrosion resistance). In one embodiment the apparatus comprises copper tubes which tubes are coated or not. The copper, on other hand, offers high heat conductivity with is useful both during regeneration and operation of the catalyst. Since it offers excellent heat conducting capability, the heat generated can be more evenly distributed and taken care of.

In one embodiment the pressure is ambient pressure. In an alternative embodiment the pressure is elevated.

The catalysts and reactors can have any of the designs known in the art for catalytically treating a fluid or gas at elevated temperatures, such as a fluidized bed reactor. In one embodiment the alcohol is injected into a heated reactor such that the alcohol is quickly volatilized into gas, and the gas passes over the catalyst. Additional reaction zones or processes may or may not also be included. For example, in some embodiments, the produced hydrocarbon blendstock, may be fractionated, distilled, or otherwise separated into narrower carbon range blendstocks. In other embodiments, the produced hydrocarbon blendstock, may be mixed with or into another hydrocarbon blendstock.

In yet other embodiments, the alcohol, prior or during contact with the catalyst, may be concentrated, purified (e.g., by distillation), or mixed with another alcohol or solvent (e.g., water). Any of the foregoing exemplary additional processes may be integrated into the instant process, typically, by interconnecting the apparatus necessary for the additional process with the apparatus necessary to practice the instant process. In one embodiment the alcohol comprises about 80 wt % ethanol and about 20 wt % glycerol.

The alcohol is in general provided in a mixture comprising at least one alcohol to be converted. The mixture is contacted with the catalyst and the reaction is conducted. After the reaction has occurred the resulting hydrocarbons are recovered.

In one embodiment the temperature in step a) is in the range 350-450° C. Too high temperature may promote coke formation and production of undesired compounds (benzene, aromatics etc.), at least for ambient pressure. In one embodiment the temperature in step a) is below 360° C.

In one embodiment atmospheric pressure of about 1 atm is used for the conversion. However, in some embodiments, an elevated pressure or reduced pressure may be used. In different embodiments, the elevated pressure may be, for example, 1.5, 2, 4, 8, 10, or 15 atm. In one embodiment the pressure is up to 100 atm. Elevated pressure is particularly suitable for compounds with higher boiling point, for instance glycerol.

In other embodiments, the pressure may be reduced to, for example, 0.5, 0.2, or 0.1 atm. If the temperature is above 550° C. the pressure should preferably be higher than 1 atm.

The second catalyst is manufactured and prepared as known catalysts within this field except that an etching step is performed before the metal loading. In one embodiment the etching step during manufacture of the second catalyst is performed under basic conditions. In one embodiment the pH during etching is above 8. In one embodiment the etching step during manufacture of the catalyst is performed with NaOH. In one embodiment the etching step during manufacture of the catalyst is performed with NaOH at a concentration in the interval 0.1 to 0.5 M. In one embodiment the etching step during manufacture of the catalyst is performed during a period in the interval from 5 minutes to 5 hours. In an alternative embodiment the etching step during manufacture of the catalyst is performed during a period in the interval from 10 minutes to 1.5 hours. A skilled person realizes that the etching can be performed using for instance a moderately alkaline solution during a long etching time or a highly alkaline solution during shorter time. In one embodiment the etching step during manufacture of the catalyst is performed at a temperature from 20-95° C. In an alternative embodiment etching step during manufacture of the catalyst is performed at a temperature from 50-90° C. After the etching step the zeolite is in one embodiment washed with water, preferably deionized water. In one embodiment the zeolite is washed until the washing solution has a neutral pH, i.e. a pH about 7 (in the interval 6.5-7.5). In one embodiment the zeolite is dried after the etching and washing steps.

The metal is loaded into the zeolite of the second catalyst after the etching step. The metal is thus loaded into the surface of the zeolite, including open pores of the zeolite. The metal is loaded for instance by providing a metal salt of the metal and exposing the salt to oxidizing conditions giving small nanoparticles on the surface of the zeolite. In one embodiment the nanoparticles comprise the metal in oxidation state +1. However, the oxidation state of metals constantly oscillates due to the presence of reductive components (hydrocarbons) in the process. Nanoparticles are in the range between 1 and 100 nanometers in diameter, measured in the longest possible dimension.

In one embodiment the metal is provided as nanoparticles comprising an oxide of the metal. In one embodiment the metal is present as an oxide in oxidation state +1.

Due to the manufacturing process the metal is applied on the surface of the etched catalyst, taking into account any open pores of the catalyst where the metal particles can enter pores.

In one embodiment the zeolite is converted to ammonia form using ion exchange with a solution comprising ammonium ions. In one embodiment the concentration of ammonium ions is in the interval 0.3 to 2 M. In one embodiment the temperature during the treatment with ammonium ions is in the interval 40-100° C. In one embodiment the treatment with ammonium ions is conducted for 4 to 36 hours. In one embodiment the treatment with ammonium ions is repeated at least once. After the treatment with ammonium ions the zeolite is in one embodiment calcined, i.e. heat treated, usually under air atmosphere.

The zeolite is in one embodiment metal loaded in a wet impregnation method. The zeolite material is dispersed in an aqueous solution where the aqueous solution comprises the desired metal ion(s). Catalysts comprising at least two metals are in one embodiment prepared using sequential impregnation. In an alternative embodiment simultaneous impregnation, co-impregnation is used.

In one embodiment the metal is an alloy of more than one metal. In one embodiment more than one alloys are used. In one embodiment combinations of pure metals and alloys are utilized as the metal. The word metal thus encompasses both pure metals as well as alloys.

Where it is stated that there is a metal in the catalyst, it is conceived that the metal can be in any form including in compounds such as metal oxides and metal complexes.

The surface of the first and second catalysts are decorated with an amount of catalytically active metal in particle form. The type and amount of catalytic metal loaded onto the surface are selected such that the resulting metal-loaded material is catalytically active, under conditions set forth above, for converting an alcohol to a hydrocarbon. A single metal or a combination of metals as well as an alloy or a combination of alloys may be loaded onto the surface. The loading of catalytic metal onto the surface can be any suitable amount, but is generally no more than about 2.5 wt %, wherein the loading is expressed as the amount of metal by weight of the material. In different embodiments, the metal loading is for example, 0.01%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5 wt %.

During several instances in the manufacturing process of the zeolite the zeolite can be calcined (i.e. heat treated in a thermal treatment step). In one embodiment after impregnating with metals the calcination functions to more firmly incorporate the impregnated metals onto the surface of the zeolite.

In one embodiment the zeolite is calcined (i.e. heat treated in a thermal treatment step) before etching as described above. In one embodiment zeolite is calcined after treatment with ammonium ions. In one embodiment the zeolite is calcined after treatment with the desired metal oxide nanoparticles. In one embodiment calcination is preceded by a drying step.

In different embodiments, the calcination is conducted at a temperature of at least 150° C., 200° C., 250° C., 300° C., 350° C., 400° C., 450° C., 500° C., 550° C., 600° C., 650° C., 700° C., 750° C., or 800° C., for a time period of, for example, 15 minutes, 30 minutes, 1 hour, 2 hours, 6 hours, 12 hours, 24 hours, 30 hours, 36 hours, or 48 hours. In one particular embodiment, the calcination is conducted at a temperature of at least 500° C. for a time period of at least two hours. In some embodiments, the calcination comprises a temperature change from a lower temperature to a higher temperature, and/or from a higher temperature to a lower temperature.

The steps for calcination are in one embodiment conducted under normal atmospheric pressure. However, in alternative embodiments, an elevated pressure (e.g., above 1 atm and up to 2, 5, or 10 atm) is employed, while in other embodiments, a reduced pressure (e.g., below 1, 0.5, or 0.2 atm) is employed. Furthermore, although the calcination is generally conducted under a normal air atmosphere, in some embodiments, an elevated oxygen, reduced oxygen, or inert atmosphere is used.

In one embodiment the zeolite is an aluminosilicate zeolite belonging to the pentasil family of zeolites. In one embodiment the zeolite is ZSM-5. The ZSM-5 zeolite is represented by the formula $Na_nAl_nSi_{96-n}O_{192}.16H_2O$, wherein $0<n<27$.

In one embodiment the alcohol comprises ethanol. In one embodiment the alcohol is a mixture comprising several alcohols wherein ethanol constitutes at least 90 wt % of the alcohols. In addition the mixture may further comprise additional substances such as water, at various concentrations. In one embodiment the alcohol comprises a primary alcohol. In one embodiment the alcohol is at least one selected from the group consisting of methanol, ethanol, propanol, n-propanol, and isopropanol. In one embodiment the alcohol comprises glycerol.

In one embodiment the fraction of hydrocarbons which are liquid at room temperature and atmospheric pressure is more than 50 wt % of all hydrocarbon(s). In one embodiment more than 50 wt % of the hydrocarbon(s) resulting from the reaction has at least 5 carbon atoms. It is preferred that the reaction yields a high fraction of hydrocarbons with many carbon atoms which are liquid and thus suitable for fuel for combustion engines.

In one embodiment the alcohol is purified before step a) to remove at least one substance selected from the group consisting a substance originating from a fermentation process, sugars, sulphur, phenols, and cell residues. For instance sulphur is unsuitable together with a catalyst comprising for instance copper or noble metals. In one embodiment the purification is performed by filtering. In particular a fermentation process gives residues of sugar which may give rise to problems in for instance the catalyst after a certain period of time at high temperature. Thus it is preferred that if the alcohol is manufactured with a fermentation process a purification step is performed before the conversion into hydrocarbons.

The method can be performed both batch-wise and continuously. Thus in one embodiment the conversion of an alcohol to hydrocarbons is a continuous process. In an alternative method the conversion of an alcohol to hydrocarbons is a batch process.

In one embodiment the $SiO_2/Al_2O_3$ ratio in the zeolite is about 23:1, however any ratio can be used with satisfactory result.

In one embodiment the amount of benzene is less than 1 wt % and polyaromatics is less than 5 wt %.

In a second aspect there is provided a hydrocarbon manufactured according to the process described above. In one embodiment the hydrocarbon is a constituent in gasoline. In one embodiment the hydrocarbon is a constituent in diesel. In one embodiment the hydrocarbon is a constituent in jet fuel. It is intended that the manufactured hydrocarbon is used as a blendstock in the fuel.

In one embodiment the hydrocarbon is ethene. The ethene can be further utilized for various purposes.

A skilled person realizes that the catalyst including the metal(s) on the catalyst surface have to be optimized for the different hydrocarbons intended to be manufactured.

EXAMPLES

In order to reach the desired levels of aromatics (below 35 vol %) and benzene content (i.e. well below 1 vol %), a two stage reactor system is utilized (two reactor beds in a series) for the production of gasoline from bio-ethanol. The reactor comprises two different catalysts whereupon the two or more reactors are maintained at different temperatures. In the first reactor the temperature range should be ranging from 300-550° C. (Unless indicated otherwise it is run at 400° C.). Higher temperatures are likely to promote undesired coke formation. The temperature range 300-550° C. serves to selectively produce mixture of olefins using Ni on $SiO_2$—$Al_2O_3$ (selective towards ethylene) and Cu on MgO modified SBA-15 (primarily selective towards butadiene some ethylene); still, other geo-type materials can be used.

For example Ni/$SiO_2$—$Al_2O_3$ produces selectively ethylene (95%) over long periods of reaction time. In the case of Cu—MgO/SBA-15, the catalyst selectively produces butadiene along with ethylene. As the next step, the mixture of olefins received from the first reactor was allowed to pass through the second catalytic bed maintained at slightly lower temperature than the first reactor (300-500° C.). Unless indicated otherwise it is run at 350° C. The catalysts applied in the second reactor was in one embodiment ZSM-5, but, the commercial ZSM-5 was subjected to several surface modification steps to control the number and strength of acid sites and the pore architecture. The post-modified ZSM-5 was used to load the active metals (bi-metallic systems). Surprisingly, the liquid product produced after the second reactor vessel contains 70 vol % aliphatic hydrocarbons. The amount of aromatic hydrocarbons obtained from the one stage reactor system (70 vol %) went down to 40 vol % while using the two-stage reactor system with tailored catalysts.

Figure 1:
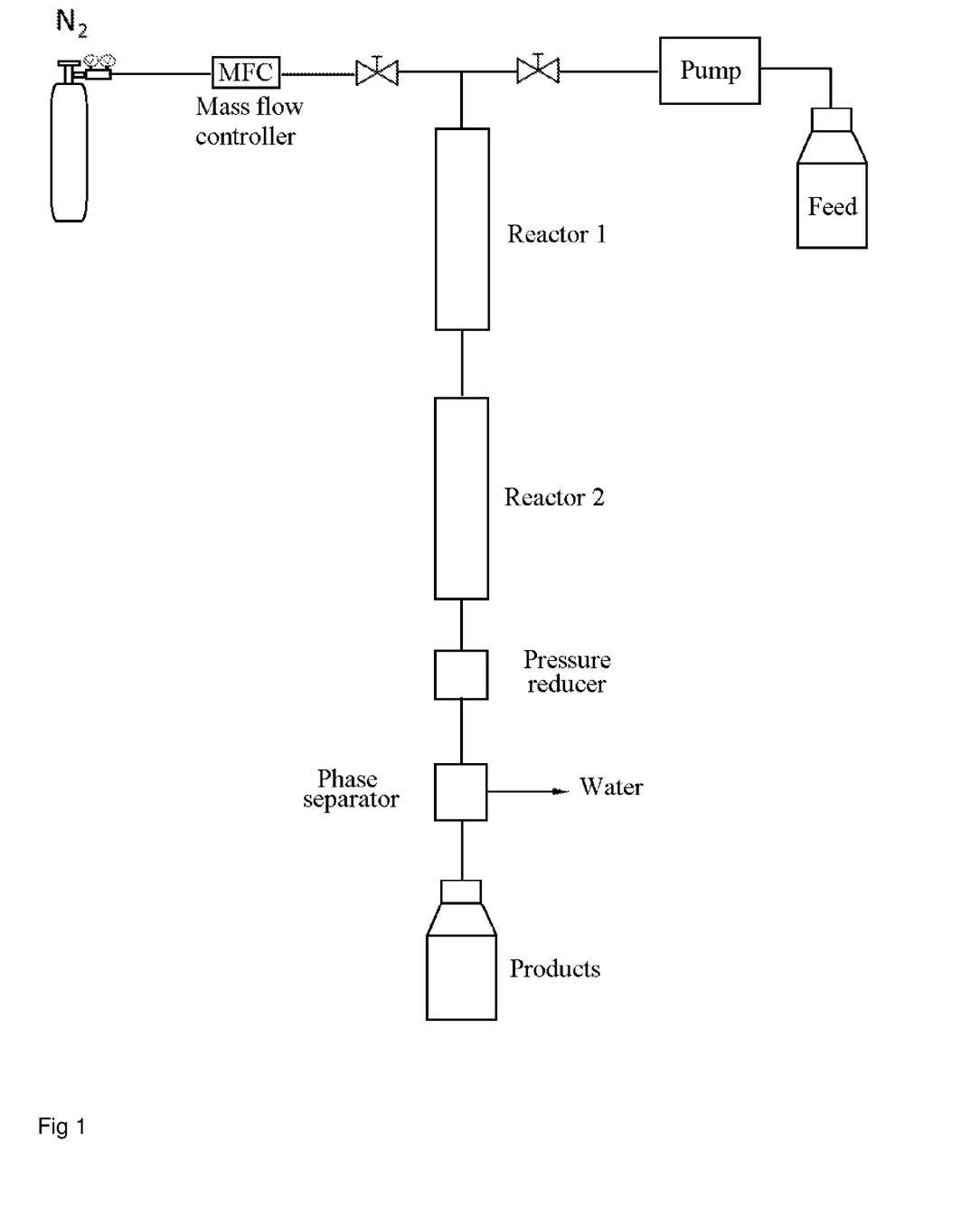
FIG. 1 schematically depicts a setup according to the invention.
Figure 2A:
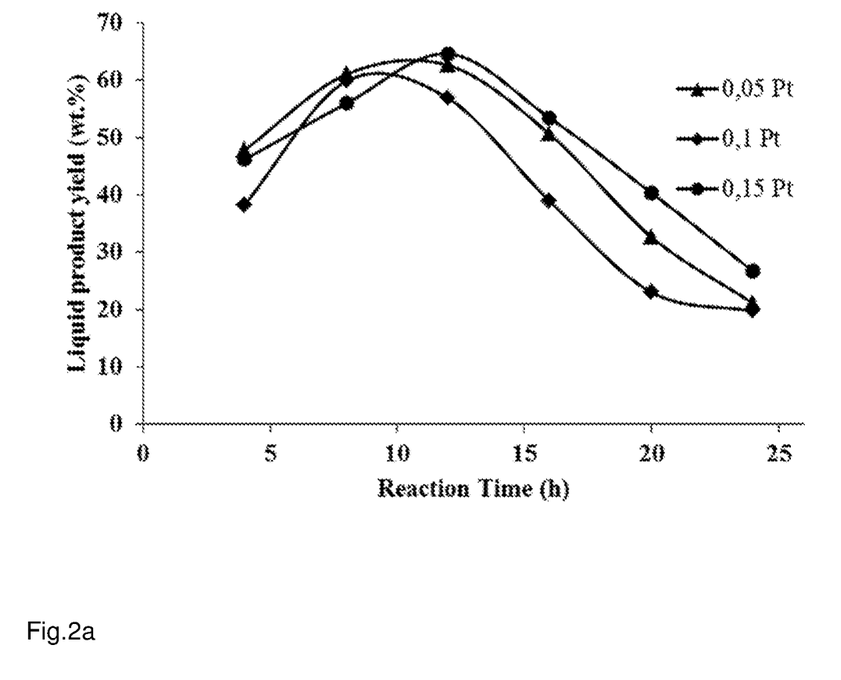
FIG. 2 shows hydrocarbon distributions over the serial catalysts.
Figure 2B:
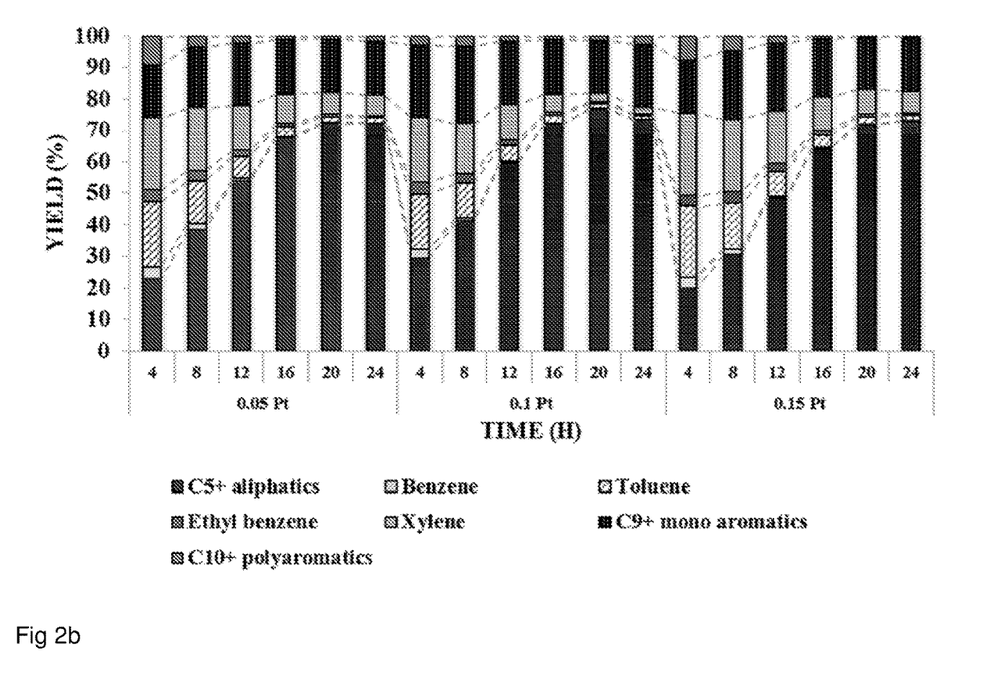

FIGS. 2a and b depict the amount of liquid hydrocarbons obtained over the different amount of metal loaded on Cu-modified desilicated ZSM-5 over the period of 24 h reaction time. The results revealed that the reaction yielded maximum of 60 wt % liquid gasoline with selectivity towards aliphatic hydrocarbons maximum of 70 wt % over all the studied catalysts. Higher Pt loading (0.15 wt %) slightly increases the stability of catalysts and the optimum of 0.1 wt % Pt (or other metal) yielded slightly more aliphatic hydrocarbons than the other catalysts. The quality of the liquid gasoline received from the two-stage system was almost similar to that of the conventional gasoline. On the other hand, the amount of benzene in the liquid product received from one-stage catalytic bed system was up to about 4.0 wt-%. Surprisingly, in the two-stage system, very low levels of benzene (at best much less than 0.1 wt-%) is easily produced (much below the allowed limit of 1.0 vol-%). Surprisingly, under optimal conditions (feed rate and temperature profile of the catalyst bed), benzene contents down to 0.05 wt % were observed. Moreover, under these conditions, on volume basis, the yields of liquid HC's and water are more or less equal but slightly more HC's are usually produced. The gaseous products obtained are mainly C3, C4 and C5 hydrocarbons and could be directly marketed (cylindered or otherwise) as LPG (liquid petroleum gas, a substitute of LNG, liquefied Natural Gas or common propane-butane mixtures named e.g. 'gasol' for gas stoves and alike) to the customers. Alternatively, this fraction can be combusted by a gas engine to produce electricity or, potentially, be recirculated into the catalytic process before the 2nd catalyst bed. At the time of catalyst deactivation, ethylene is the major component that can be observed, indicating that the catalyst deactivation in the 1st bed is clearly slower. These are the preliminary results achieved upon successful conversion of ethanol into gasoline fuel range hydrocarbons an par with the requirements of current fuel standards. On the other hand, the two-stage system also produces the same yield of liquid gasoline (about 60 wt %) in comparison with the single-stage reaction system.

Figure 3A:
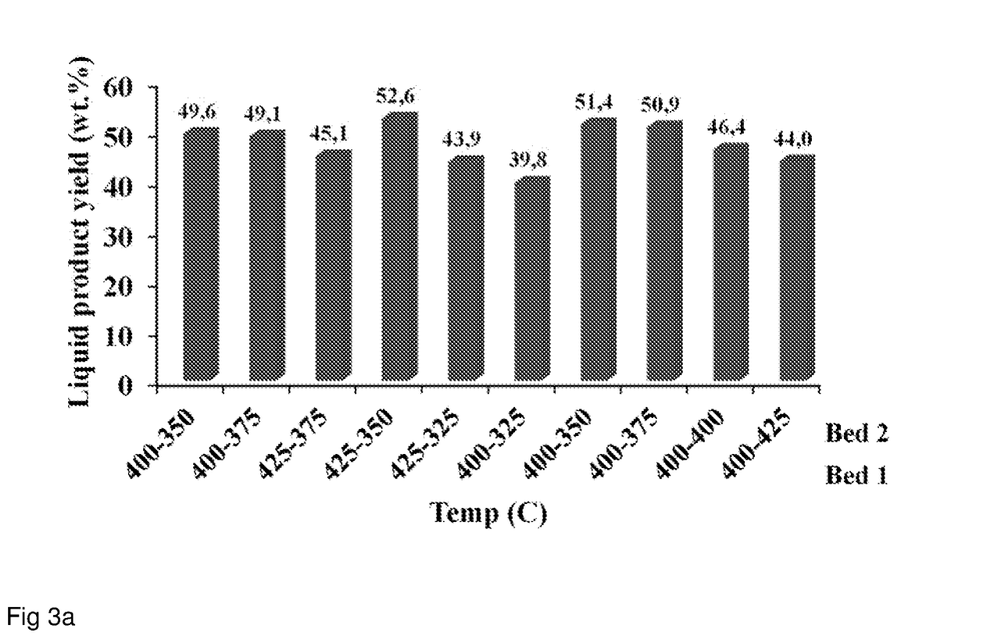
FIG. 3 shows hydrocarbon distributions over the serial catalysts (two consecutive catalyst beds in series) at different temperatures. However, the temperatures can also be equal in the two beds.
Figure 3B:
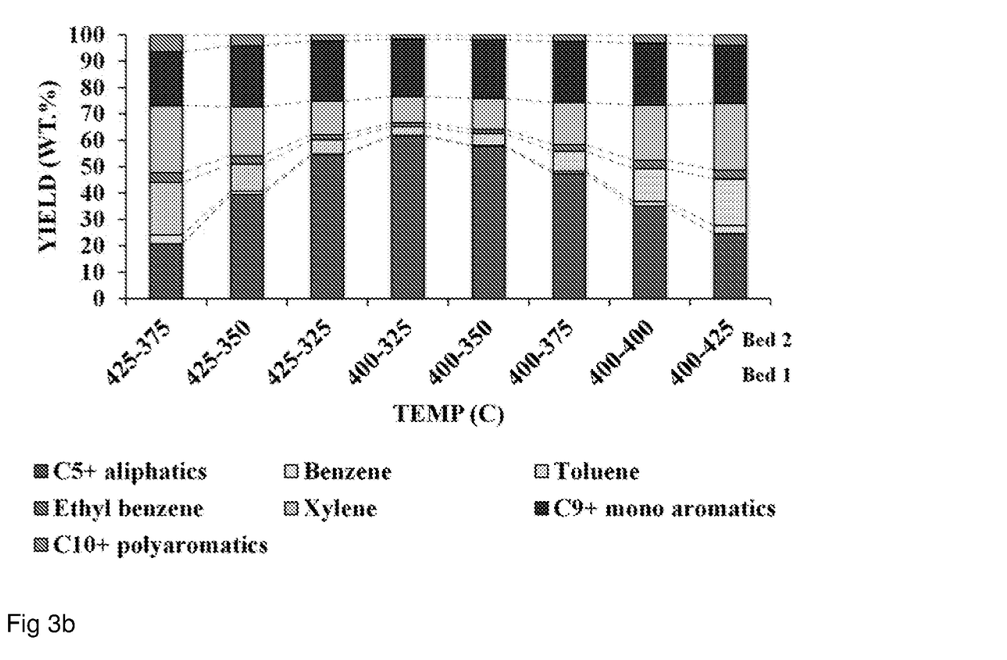
Figure 4A:
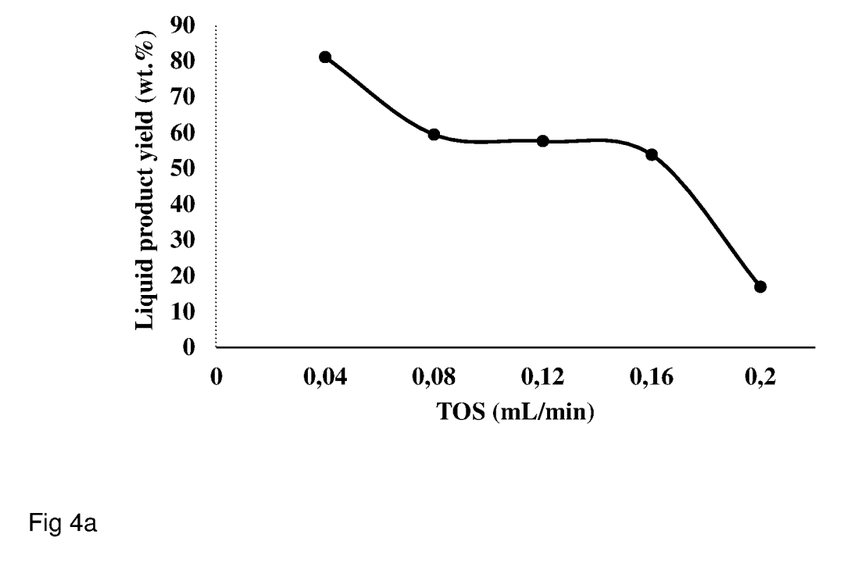
FIG. 4 shows hydrocarbon distributions over serial catalysts at different flow rates.
Figure 4B:
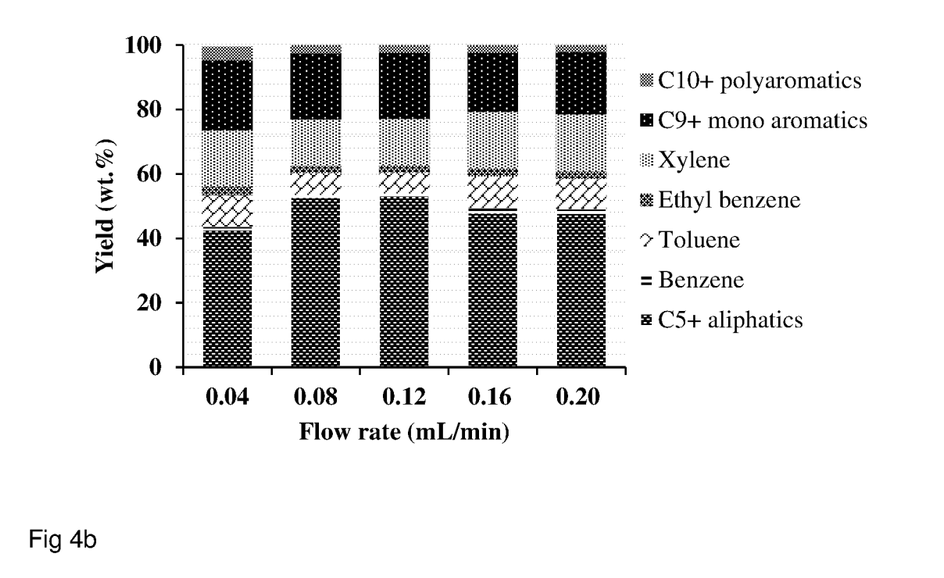
Figure 5:
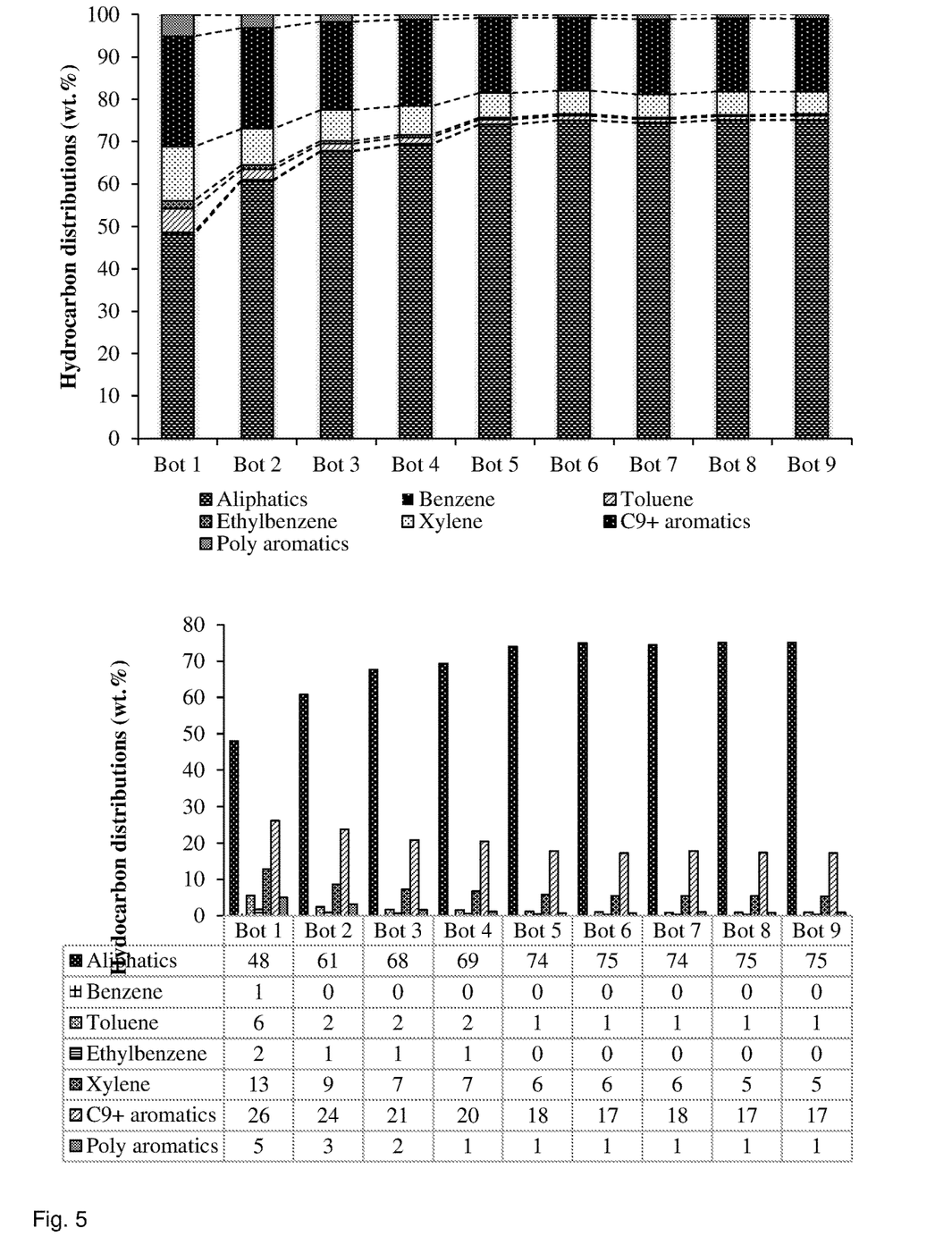
FIG. 5 shows an analysis of products for various samples. 'Bot' indicates sample withdrawn at increasing time-on-stream.
Figure 6:
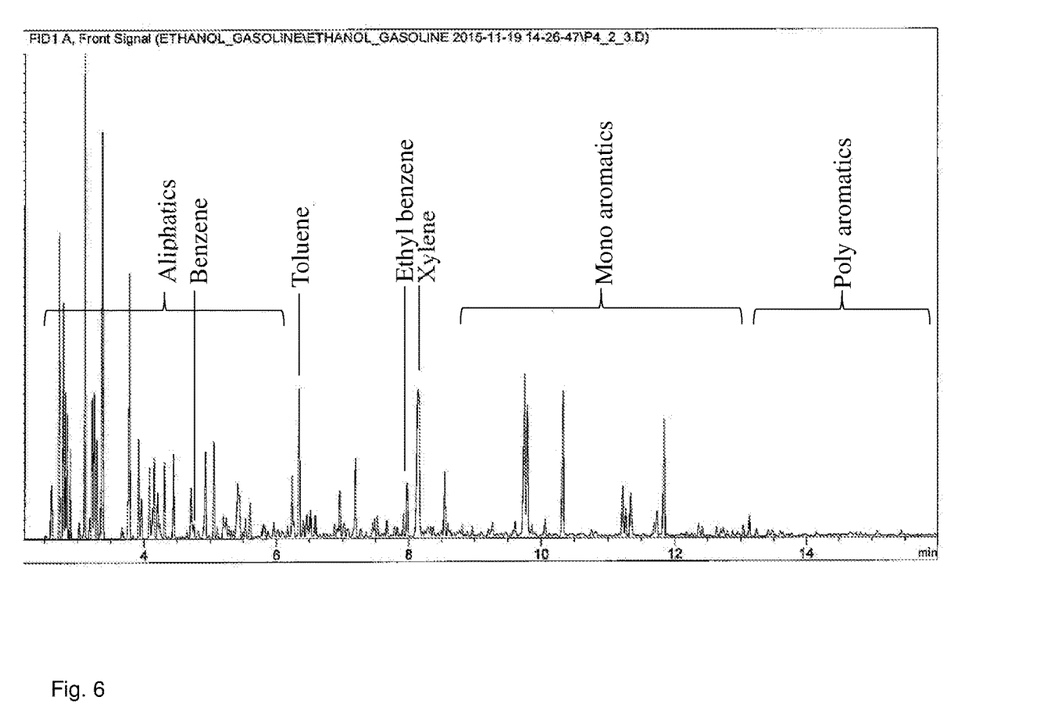
FIG. 6 shows an analysis result from a sample.
Figure 7:
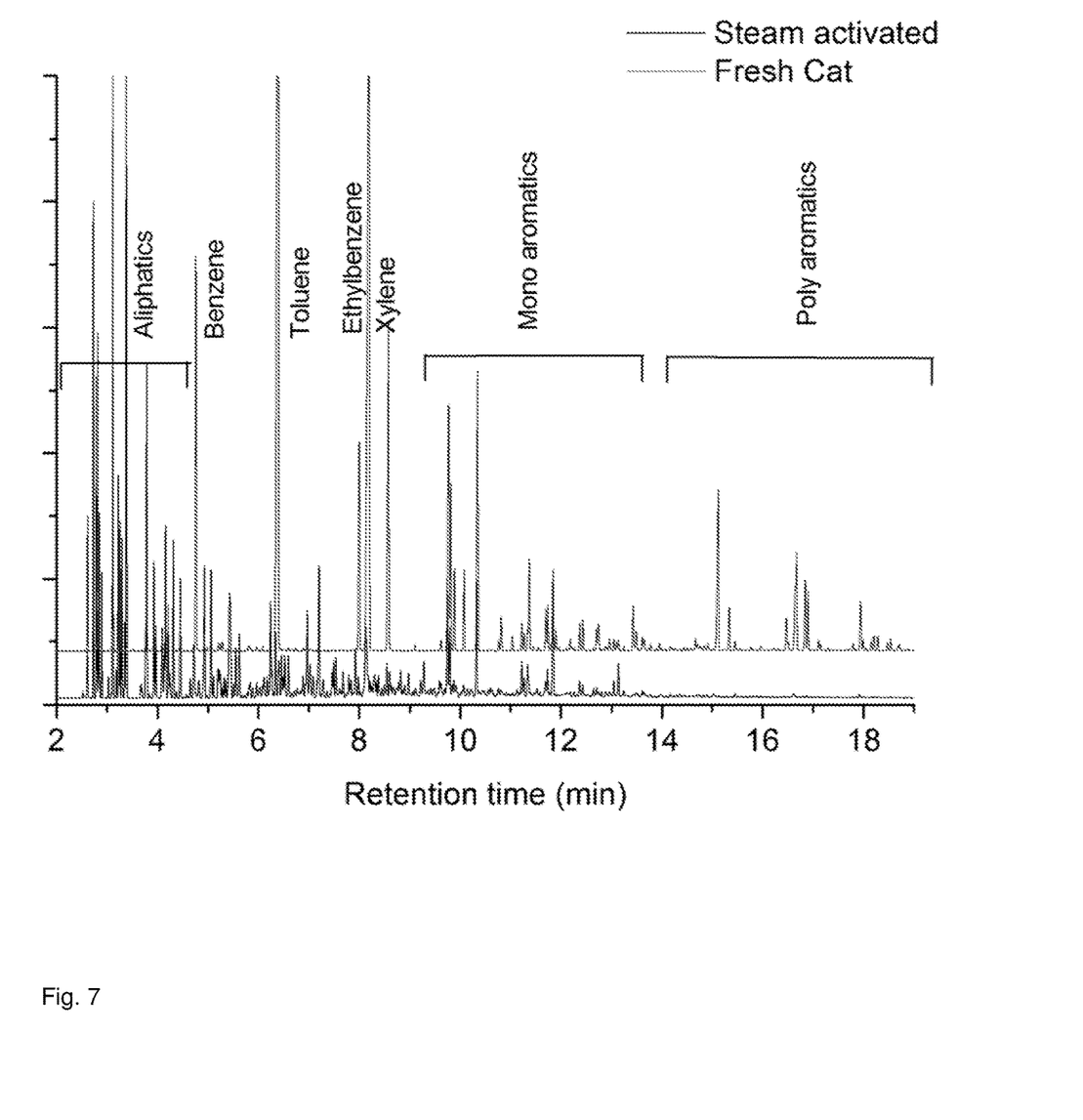
FIG. 7 shows an analysis result from a sample.
Figure 8:
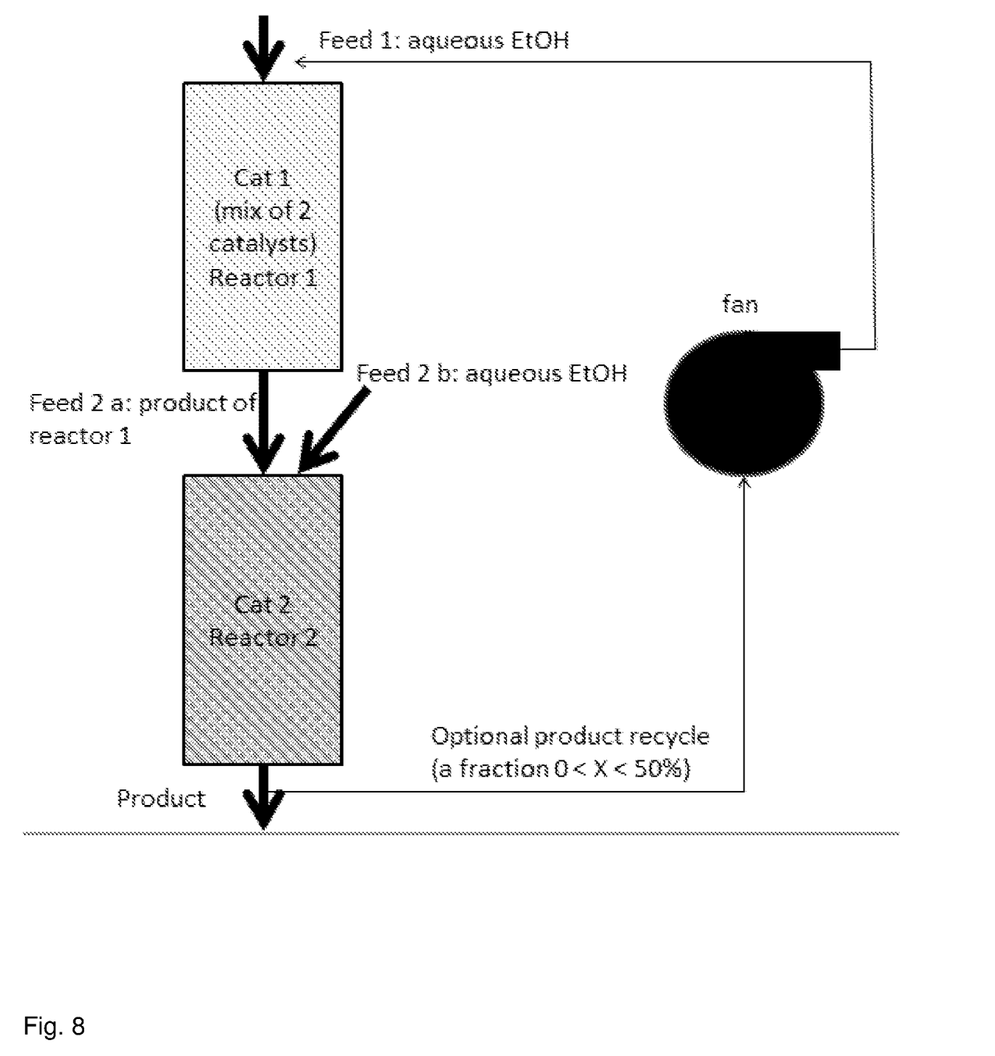
FIG. 8 shows a setup according to the invention with two reactors in series with recycling to the first catalyst and an additional feed of alcohol to the second catalyst. A fan/pump is recycling a fraction of the product.

The influence of different temperatures on both catalytic bed was studied with the temperatures ranging from 325-425° C. and the results are presented in FIGS. 3a and b, respectively. From the results it was observed that the temp of 300-425° C. at the first bed and the temp of 350-375° C. yielded a higher amount of liquid hydrocarbons than the other temperatures studied. However, the temp at the second bed about 325° C. produced slightly more aliphatic hydrocarbons, very little amount of benzene (0.3 wt %) than the other studied temperatures. Interestingly, the amount of benzene, toluene, and xylene (BTX) formation is dependent of the temperatures over these catalysts and produced least amount of these compounds at lower temperatures (bed 1, 400° C.; bed 2, 325° C.). On the other hand, the amount of C9+ aromatics formation is independent of the temperature and produced constant amount of C9+ compounds over all the studied temperatures. In order to understand the influence of ethanol flow rate, different flow rates ranging from 0.04-0.20 mL/min were studied and the results were presented in FIGS. 4 a and b. From the results it can be observed that the lower flow rate (0.04 mL/min) produced maximum of 80% liquid products and doubling of the flow rate slightly decreases the liquid product yield; however, further increase in flow rate up to 0.16 mL/min produced the same amount of liquid products and decreased rapidly at further increase of the flow rate (0.2 mL/min). On the other hand, reasonable amount of aliphatic hydrocarbons were produced on the moderate flow rate ranging from 0.08-0.12 mL/min and produce less amount of BTX. From the reaction parameters optimization, we concluded that the temperature ranging from 325-425° C., the ethanol flow rate 0.08-0.12 mL/min and the optimum of second metal (Pt) 0.1 wt % on the catalyst surface produced the gasoline, in essence, similar to or better that of the quality of commercial gasoline.

Catalyst Characterization 2-Stage System—X-Ray Powder Diffraction (XPS) for the Surface Composition In the current formulation we have also 0.1 wt-% Pt addition in the Cu modified ZSM-5. Also, the ZSM-5 was desilicated by alkali treatment as earlier. In terms of Pt loading, we have found out that 0.2 wt-% is too much and 0.05 wt-% is too little. 0.15 wt-% gives better result. In summary, the optimal Pt amount should be 0.05<X<0.2 wt-%.

The results of the XPS indicate that we most likely have mixed $Cu_2O/CuO$ oxide phases while the Pt loading is too low (below the instrument sensitivity) to be quantified. Nevertheless, it is likely that Pt at least partially alloys with Cu but definitely alters the electronic stage of the surface. We can perhaps speculate that Pt which is rather readily (re-)reduced by contact with the substrate (hydrocarbon) stream, helps to maintain Cu on less oxidized state than in the absence of the Nobel metal. Still, Au additions in similar concentrations as Pt might give good results since Au is very difficult to oxidize. In this folder, also the XPS data is enclosed. When looking at the spectra obtained for the fresh as well as spent and regenerated catalysts (both beds), no major changes can be seen indicating that the catalyst materials should be rather durable and possible to reuse through a multitude of deactivation-regeneration cycles.

Other features and uses of the invention and their associated advantages will be evident to a person skilled in the art upon reading the description and the examples.

It is to be understood that this invention is not limited to the particular embodiments shown here. The embodiments are provided for illustrative purposes and are not intended to limit the scope of the invention since the scope of the present invention is limited only by the appended claims and equivalents thereof.

The invention claimed is:

1. A method for converting ethanol to hydrocarbons, said method comprising the steps of:
   a) contacting ethanol with a first catalyst on a carrier, wherein said carrier is a mixed oxide carrier, said first catalyst comprises Ni, and optionally at least one selected from the group consisting of metals and metal oxides,
   b) contacting a resulting mixture from step a), said mixture comprising ethylene, with a second catalyst, wherein said second catalyst is an etched ZSM-5 catalyst loaded with Cu and Pt, wherein the etched metal-loaded ZSM-5 catalyst is manufactured with a method comprising a step of etching ZSM-5 catalyst with subsequent loading of Cu and Pt onto the etched ZSM-5 catalyst, wherein the Cu and Pt are in the form of nanoparticles, and
   c) recovering the hydrocarbons resulting from a reaction in step b), wherein the hydrocarbons resulting from the reaction in step b) comprise alkanes containing four to twenty carbon atoms, less than 1 wt % benzene, and less than 35 vol % aromatics.

2. The method according to claim 1, wherein the temperature in step a) is in the range of 300-550° C.

3. The method according to claim 1, wherein the temperature in step b) is in the range of 300-500° C.

4. The method according to claim 1 wherein an amount of ethanol is added to the resulting mixture from step a).

5. The method according to claim 1 wherein an amount of a resulting mixture from step b) is recirculated to at least one selected from the first catalyst and the second catalyst.

6. The method according to claim 5, wherein the resulting mixture from step b) is recirculated in a fraction of 1-50 wt % calculated on the resulting mixture from step b).

7. The method according to claim 1, wherein the etching step during manufacture of the second catalyst is performed under basic conditions with a pH above 8.

8. The method according to claim 1, wherein the etching step during manufacture of the second catalyst is performed with NaOH.

9. The method according to claim 1, wherein the etching step during manufacture of the second catalyst is performed during a period of from 5 minutes to 5 hours.

10. The method according to claim 1, wherein the etching step during manufacture of the second catalyst is performed at a temperature of from 20-95° C.

11. The method according to claim 1, wherein the ethanol is purified before step a) to remove at least one substance selected from the group consisting of a substance originating from a fermentation process, sugars, sulphur, phenols, and cell residues.

12. The method according to claim 1, wherein the conversion of ethanol to hydrocarbons is a continuous process.

13. The method according to claim 1, wherein the conversion of ethanol to hydrocarbons is a batch process.

14. The method according to claim 1, wherein at least one of the first catalyst and the second catalyst is regenerated.

15. The method according to claim 1, wherein the first catalyst is residing in a first part of a compartment and wherein the second catalyst is residing in a second part of the same compartment and wherein first and second parts are located so that the ethanol first comes into contact with the first catalyst and then comes into contact with the second catalyst.

16. The method according to claim 1, wherein the temperature in step a) is in the range of 350-450° C.

17. The method according to claim 1, wherein the temperature in step b) is in the range of 300-400° C.

18. The method according to claim 1, wherein the hydrocarbons resulting from the reaction in step b) comprise less than 0.1 wt % benzene.

19. The method according to claim 1, wherein the method is conducted at atmospheric pressure.

20. The method according to claim 1, wherein the hydrocarbons resulting from the reaction in step b) comprise more than 50 wt % hydrocarbons having at least 5 carbon atoms.

\* \* \* \* \*